United States Patent [19]

Burd

[11] Patent Number: 5,518,930

[45] Date of Patent: May 21, 1996

[54] SIMULTANEOUS CUVETTE FILLING WITH MEANS TO ISOLATE CUVETTES

[75] Inventor: Tammy L. Burd, Fremont, Calif.

[73] Assignee: Abaxis, Inc., Sunnyvale, Calif.

[21] Appl. No.: 379,424

[22] Filed: Jan. 27, 1995

Related U.S. Application Data

[62] Division of Ser. No. 115,163, Sep. 1, 1993, Pat. No. 5,409,665.

[51] Int. Cl.⁶ ........................................... G01N 21/05
[52] U.S. Cl. ..................... 436/45; 422/64; 422/72; 436/177; 494/17
[58] Field of Search ................... 436/45, 43, 174, 436/177, 807, 809; 422/64, 72, 68.1, 100, 102; 210/787, 789, 360.1; 494/17, 16

[56] References Cited

U.S. PATENT DOCUMENTS

| | | | |
|---|---|---|---|
| 3,890,101 | 6/1975 | Tiffany et al. | 422/72 |
| 4,244,916 | 1/1981 | Guigan | 422/72 |
| 4,314,968 | 2/1982 | Guigan | 422/64 |
| 4,381,072 | 4/1983 | Matsumoto et al. | 494/10 |
| 4,623,519 | 11/1985 | Cornut et al. | 422/72 |
| 4,761,268 | 8/1988 | Andersen et al. | 422/72 |
| 4,847,205 | 7/1989 | Burtis et al. | 436/45 |
| 4,894,204 | 1/1990 | Cornut | 422/72 |
| 4,902,479 | 2/1990 | Bri kus | 422/72 |
| 4,963,498 | 10/1990 | Hillman et al. | 436/69 |
| 5,061,381 | 10/1991 | Burd | 210/789 |
| 5,071,625 | 12/1991 | Kelln et al. | 422/72 |
| 5,077,013 | 12/1991 | Guigan | 422/64 |
| 5,122,284 | 6/1992 | Braynin et al. | 210/782 |
| 5,160,702 | 11/1992 | Kopf-Sill et al. | 422/72 |
| 5,242,606 | 9/1993 | Braynin et al. | 210/787 |
| 5,242,803 | 9/1993 | Burtis et al. | 435/7.92 |
| 5,256,376 | 10/1993 | Callan et al. | 422/102 |

*Primary Examiner*—Jill Warden
*Assistant Examiner*—Long V. Le
*Attorney, Agent, or Firm*—Townsend and Townsend and Crew

[57] ABSTRACT

The present invention provides centrifugal rotors for delivering a liquid, typically a biological sample such as diluted plasma, to a plurality of cuvettes in the rotor. The cuvettes are positioned radially inward of an annulate manifold and are connected to the manifold through a plurality of inlet channels. The liquid is introduced in one end of the manifold and, as the rotor spins, the liquid fills the manifold from the radially outward edge inward. After, the manifold fills, the liquid flows radially inward through the inlet channels into the chambers. The design allows the simultaneous filling of the cuvettes. The inlet channels may also be sized such that as liquid enters the cuvettes, gas escapes through the inlet channel.

13 Claims, 6 Drawing Sheets

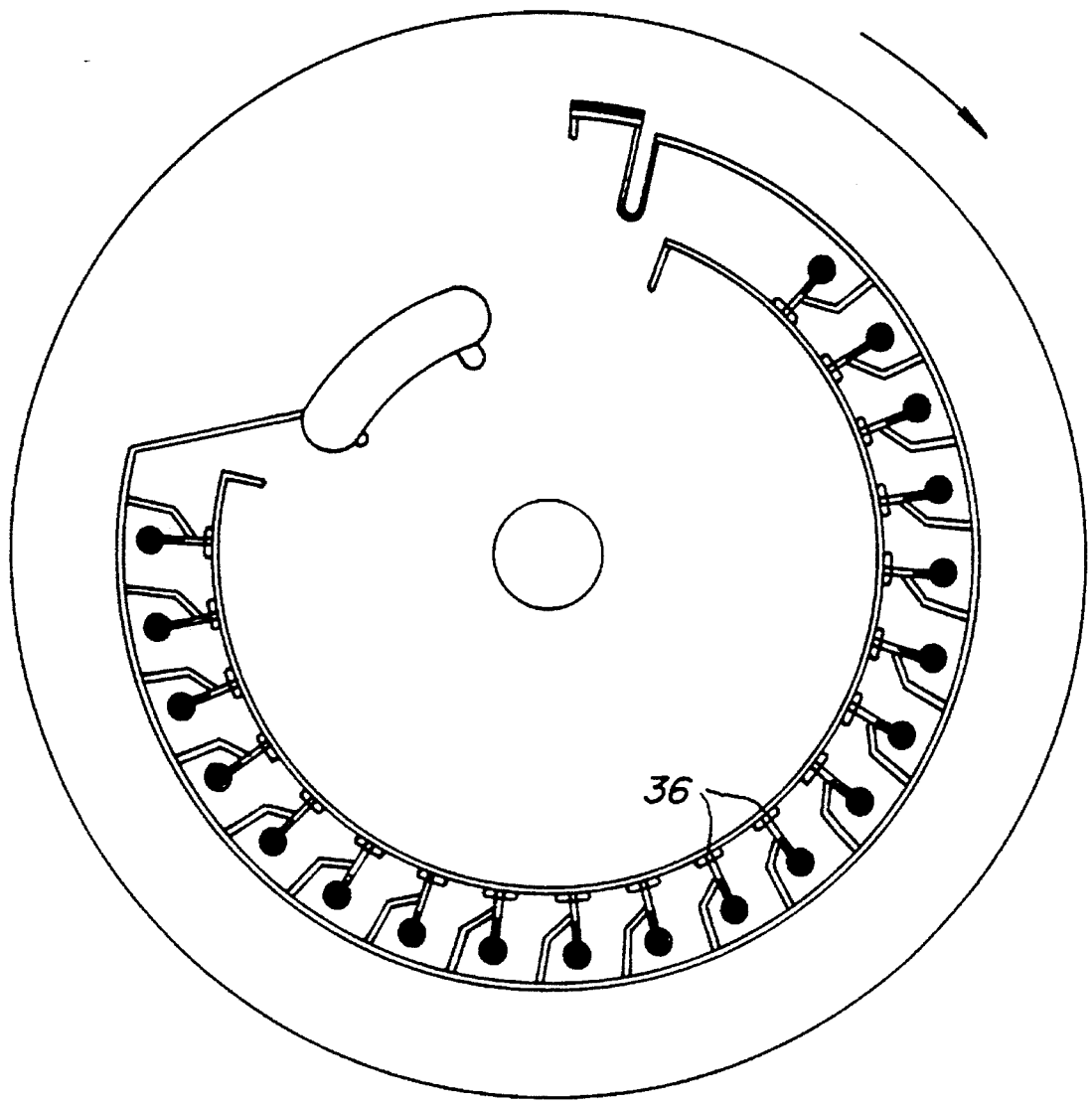
FIG. IE.

SIMULTANEOUS CUVETTE FILLING WITH MEANS TO ISOLATE CUVETTES

This is a division of application Ser. No. 08/115,163, filed Sep. 1, 1993, now U.S. Pat. No. 5,409,665.

BACKGROUND OF THE INVENTION

The present invention relates generally to devices and methods for analyzing biological fluids. In particular, it relates to the design and use of improved centrifugal rotors which allow delivery of a biological sample or reagent to a cuvette or other chamber in the rotor.

Biological tests of blood plasma and other biological fluids frequently require that fluids be quickly divided into predetermined volumes for analysis in a variety of optical tests or assays. It is also frequently desirable to separate potentially interfering cellular components of the material from the biological fluid prior to testing. Such measurement and separation steps have previously been typically performed by centrifugation to separate, for instance, blood plasma from the cellular components, followed by manual or automated pipetting of predetermined volumes of the blood plasma into separate test wells. Such procedures are labor intensive and time-consuming. As a result, various automated systems and methods have been proposed for providing multiple aliquots of plasma suitable for testing in a more efficient manner.

A major advance in the analysis of biological fluids has been the use of centrifugal rotors. These rotors are designed to measure volumes of a biological fluid, such as blood, remove cellular components, and mix the fluid with an appropriate diluent for optical testing. Typically, the rotors provide a plurality of discrete volumes of sample in separate cuvettes in which the sample is optically analyzed.

When the cuvettes are filling, it is important that individual cuvettes are completely isolated so that bubbles or chemical debris from one cuvette cannot be transferred to another. Simultaneous or parallel filling of the cuvettes is often desired, particularly when chemical analyses depend upon reaction rate.

The rotors capable of performing these functions should be capable of measuring and distributing relatively small volumes of liquid to a large number of cuvettes. The rotor design should be simple and amenable to low-cost manufacturing procedures. In particular, it is desirable for the rotors to be of unitary construction with no separable or movable parts. Liquid measurement and separation steps should be simple and take place in relatively short times. In particular, the methods should require relatively few steps and should be capable of being performed with little or no intervention or manipulations by the operator. It would be particularly desirable if the methods required only rotation of the rotor in order to effect measurement and delivery of the liquid. The present invention addresses these and other needs.

DESCRIPTION OF THE BACKGROUND ART

U.S. Pat. No. 4,244,916 discloses a rotor comprising a plurality of cuvettes positioned radially outward of a central receptacle. Each cuvette is connected to the central receptacle by a duct and comprises a separate air escape orifice. U.S. Pat. No. 4,314,968 relates to rotors having cells positioned on the periphery of the rotor. Each cell includes a peripheral orifice for removing fluid introduced into the cell. U.S. Pat. No. 4,902,479 discloses a multi-cuvette rotor comprising elongated, radially extending cuvettes. Each elongated cuvette comprises a first chamber for receiving a first constituent and a second chamber for receiving a second constituent. A divider structure between the first and second chambers prevents mixing of the constituents before a predetermined time. Mixing occurs as the rotor is spun at a sufficient speed. U.S. Pat. No. 4,963,498 discloses devices which rely upon capillaries, chambers, and orifices to pump and mix fluids for optical analysis. U.S. Pat. No. 5,077,013 discloses rotors comprising peripheral cuvettes connected to holding chambers positioned radially inward from the cuvettes.

SUMMARY OF THE INVENTION

The present invention provides centrifugal rotors for delivering a liquid, typically a biological sample such as diluted plasma, to a plurality of chambers in the rotor. The chambers are then used to perform any of a number of functions, such as metering liquids, separating solid components from a sample, or analysis of the sample. In the preferred embodiments, the chambers are cuvettes comprising reagents for the optical analysis of the sample.

In the rotors of the invention the chambers are positioned radially inward of an annulate manifold and are connected to the manifold through a plurality of inlet channels. The liquid is introduced in one end of the manifold and, as the rotor spins, the liquid fills the manifold from the radially outward edge inward. After the manifold fills, the liquid flows radially inward through the inlet channels into the chambers.

In the preferred embodiments, each inlet channel has a generally U-shaped bend so that the liquid flows first generally radially inward through the inlet channels to the bend and then generally radially outward into the chambers. The relative placement of the U-shaped bend in each inlet channel can be used to determine the order in which the chambers are filled. If simultaneous or parallel filling is desired, the U-shaped bend of each inlet channel is positioned at the same radial distance from the axis of rotation. If a particular order in which the cuvettes are filled is desired, the position of the U-shaped bend of each inlet channel can be adjusted accordingly. Those cuvettes connected to inlet channels having bends spaced farther from the axis of rotation will fill before those having channels with bends spaced closer to the rotor.

The liquid may be delivered to the manifold in a variety of ways. It can be applied by the operator directly to a port connected to the manifold or be delivered to the manifold from another chamber within the rotor, as long as there is some means for controlling the flow rate of the liquid entering the manifold. Typically, the liquid is delivered through a feeding channel connected to a sample reservoir positioned radially inward of the manifold. The feeding channel can be generally straight, curved or can be a siphon. To ensure simultaneous filling (i.e., parallel rather than serial filling) of the chambers, the flow rate in the feeding channel must be low enough to allow the manifold to fill from the outer radius inward.

One of skill will recognize that resistance to flow in a given channel is one of the factors that will affect the flow rate in a channel. Resistance to flow will depend upon the liquid being transported through the channel. Resistance to flow of liquid in the channel can be adjusted in a number of ways. Typically, the geometry of the passage is used. Channels having a smaller cross section (as determined by width and/or depth) have greater resistance than those with larger cross sections. Also, lengthening a channel increases resistance to flow. Alternatively, the surface texture of the channel can be modified to increase or decrease resistance to flow.

To remove excess liquid in the manifold and inlet channels after the chambers have filled, an excess liquid dump is positioned radially outward of the manifold and is connected to the manifold through an excess liquid channel. The excess liquid channel is connected to the end of the manifold opposite the end into which liquid is introduced.

Usually the excess liquid channel is a siphon. The siphon is designed such that the excess liquid is not removed from the manifold until after the cuvettes are filled. In particular, the elbow of the siphon is positioned radially inward of each U-shaped bend in the inlet channels to prevent priming of the siphon before the cuvettes are filled. As the cuvettes are filling, the liquid in the siphon does not flow past the elbow because the liquid finds a radial position equal to the U-shaped bends in the inlet channels. If the inlet channels are connected to a channel extending radially inward (e.g., a venting channel) the liquid continues travelling radially inward past the U-shaped bends after the cuvettes are filled. This allows the liquid to flow just past the elbow of the siphon and the siphon is "primed". As the rotor spins, the combination of centrifugal and capillary forces draw the excess liquid out of the manifold into the excess liquid dump. To ensure the siphon gets primed and stays primed during the emptying process, the flow rate in the siphon must be smaller than the flow rate of liquid being fed into the siphon. In addition, the end from which liquid is removed from the manifold is slightly farther from the center of the rotor than the other end.

The rotors of the invention will also typically comprise a venting manifold positioned radially inward of the chambers and venting channels connecting each chamber to the venting manifold. The venting manifold can be positioned radially inward of the level of liquid in the sample reservoir, thus ensuring that liquid does not flow into the venting manifold, when the manifold is filling faster than it is emptying. If the venting manifold is positioned radially outward of the liquid level in the sample reservoir, a pocket for holding excess liquid can be positioned radially inward of each chamber. The pockets are sized to accommodate any residual liquid in the reservoir and thus prevent liquid from flowing into the venting manifold. The pockets provide a holding area for the liquid until the siphon removes it.

In some preferred embodiments, the axis of rotation of the annulate manifold is positioned away from the axis of rotation of the rotor. Typically, the end from which liquid is removed from the manifold is slightly farther from the center of the rotor than the other end. This design ensures complete emptying of the manifold. Usually, the increase in radius from the beginning of the manifold to the end of the manifold is between about 0.1 mm to about 1.5 mm or more, preferably between about 0.5 mm and about 1 mm.

BRIEF DESCRIPTION OF THE DRAWINGS

FIGS. 1A–E are top plan views of the centrifugal rotor of the present invention showing progressive stages of the movement of liquid through the chambers and channels of the rotor.

DESCRIPTION OF THE PREFERRED EMBODIMENT

Figure 1A:
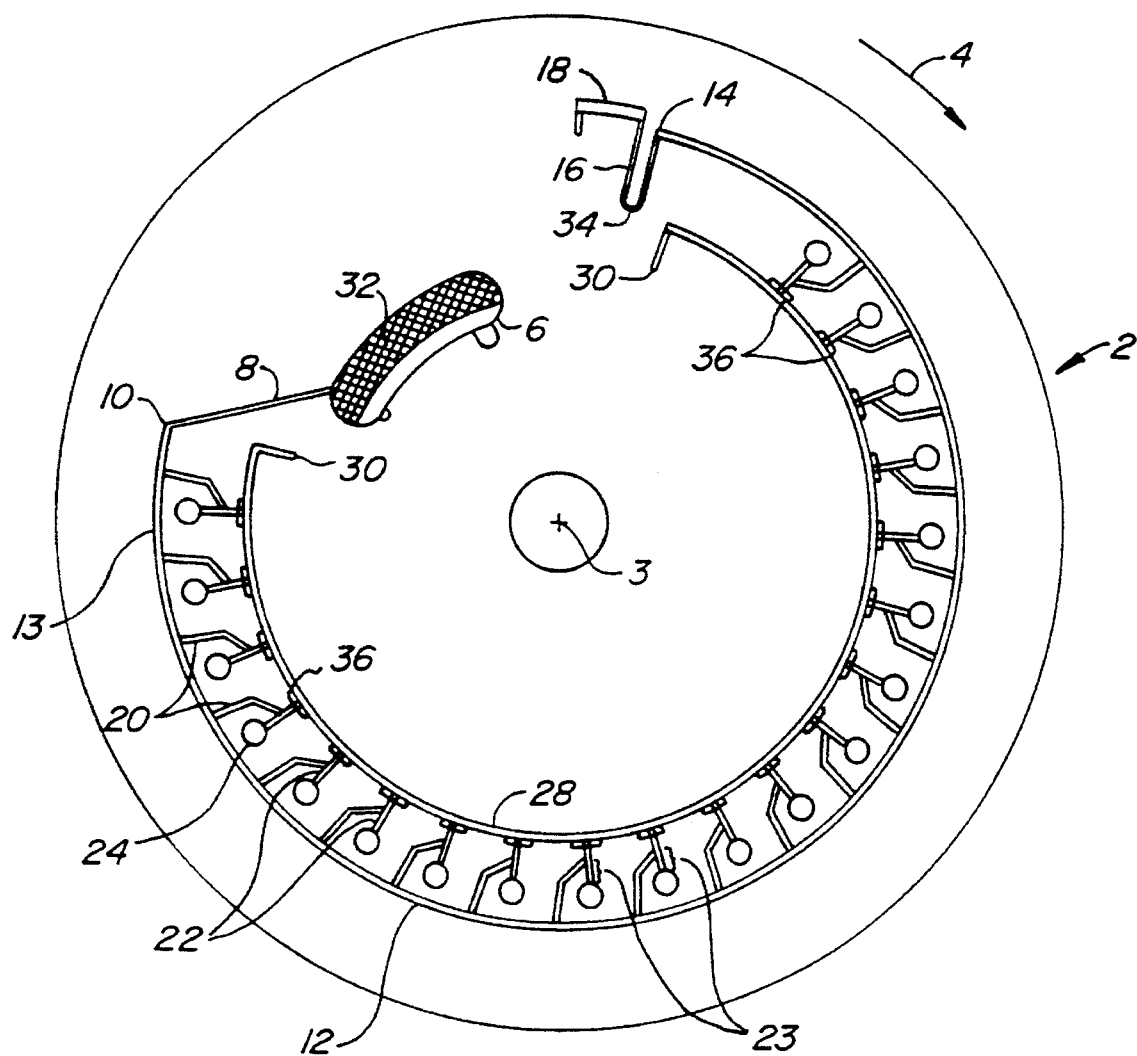

The present invention provides methods and devices for the delivery of liquids to chambers in an analytical rotor. The rotors of the invention are designed such that the cross contamination between chambers is minimized and the order in which the cuvettes are filled can be predetermined. Typically, the chambers fill simultaneously, to increase accuracy in analytical procedures involving chemical reaction rates.

The rotors of the invention are suitable for the analysis of any liquid, typically a biological sample such as whole blood or plasma. It is also useful with numerous other biological fluids, such as urine, sputum, semen, saliva, ocular lens fluid, cerebral fluid, spinal fluid, amniotic fluid. Other fluids that can be tested include tissue culture media, food and industrial chemicals, and the like.

The rotors typically provide chambers which can separate cellular components from the biological sample (e.g. whole blood), measure a precise volume of liquid sample (e.g. plasma), mix the sample with an appropriate diluent and deliver the diluted sample to cuvettes for optical analysis. The fluid delivered to the cuvettes, undergoes reaction(s) within the cuvettes, e.g., reaction with a reagent which forms part of an analytical procedure to detect one or more analytes within the fluid. The sample may further be optically analyzed while present in the rotor, either with or without prior reaction.

The apparatus of the present invention comprises an analytical rotor having a rotor body which is capable of being mounted on a conventional laboratory centrifuge of the type which is commercially available from suppliers, such a Beckman Instruments, Inc., Spinco Division, Fullerton, Calif.; Fisher Scientific, Pittsburgh, Pa.; VWR Scientific, San Francisco, Calif., and the like. Generally, the centrifugal rotor will include a receptacle or other coupling device suitable for mounting on a vertical drive shaft provided by the centrifuge. The particular design of the receptacle or coupling device will depend on the nature of the centrifuge, and it will be appreciated that the centrifugal rotor of the present invention may be adapted for use with all or most types of centrifuges which are now available or which may become available in the future.

The rotor body comprises a structure which maintains a desired geometric pattern or relationship between a plurality of chambers, interconnecting passages, and vents, as described in more detail below. Various specialized chambers and channels suitable for use in the rotors of the invention are disclosed in U.S. Pat. Nos. 5,061,381, 5,122,284, and 5,186,844 and U.S. Ser. No. 07/783,041, now U.S. Pat. No. 5,242,606, which are incorporated herein by reference.

Usually, the body will be a substantially solid plate or disk with the chambers and passages formed as spaces or voids in the otherwise solid matrix. Conveniently, such solid plate structures may be formed by laminating a plurality of separately-formed layers together into a composite structure where the chambers and horizontal passages are generally formed between adjacent layers. The vertical passages may be formed through the layers. The individual layers may be formed by injection molding, machining, or combinations thereof, and will usually be joined together, typically using a suitable adhesive or by ultrasonic welding. The final enclosed volumes are formed when the layers are brought together.

Of course, the centrifugal rotor could also be formed as a plurality of discrete components, such as tubes, vessels, chambers, etc., arranged in a suitable framework. Such assemblies of discrete components, however, are generally more difficult to manufacture and are therefore less desirable than those formed within a substantially solid plate.

The rotor body may be formed from a wide variety of materials and may optionally include two or more materials. Usually, the material(s) will be transparent so that the presence and distribution of the biological fluid, cellular components, and reagents, may be observed within the various internal chambers and passages. Optionally, to the extent analytical chambers, e.g., cuvettes, or other test wells are formed within the rotor, it is desirable to have suitable optical paths formed within the rotor so that the contents of the cuvettes may be observed spectrophotometrically, fluorometrically, or by other optical assessment instruments. The construction of suitable cuvettes having particular optical paths formed therethrough is disclosed in U.S. Pat. No. 5,173,193, the disclosure of which is incorporated herein by reference. In the preferred embodiment, the rotor is formed with an acrylic resin having suitable optical properties, at least in those areas which define an optical path.

The apparatus and method of the present invention are suitable for performing a wide variety of analytic procedures and assays which are beneficially or necessarily performed on blood plasma. The analytic procedures may require that the blood plasma be combined with one or more reagents so that some visibly detectable change occurs in the plasma which may be related to the presence and/or amount of a particular component (analyte) or characteristic of the plasma. Preferably, the plasma will undergo a reaction or other change which results in a change in color, fluorescence, luminescence, or the like, which may be measured by conventional spectrophotometers, fluorometers, light detectors, etc. In some cases, immunoassays and other specific binding assays may be performed within the cell-free fluid collection chamber or within cuvettes which are connected to the collection chamber. Generally, such assay procedures should be homogenous and not require a separation step. In other cases, however, it may be possible to accommodate heterogenous assay systems by providing a means to separate blood plasma from the collection chamber or another test well or cuvette after the immunological reaction step has occurred.

Conventional blood assays which may be performed include glucose, lactate dehydrogenase, serum glutamic-oxaloacetic transaminase (SGOT), serum glutamic-pyruvic transaminase (SGPT), blood urea (nitrogen) (BUN), total protein, alkalinity, phosphatase, bilirubin, calcium, chloride, sodium, potassium, magnesium, and the like. This list is not exhaustive and is intended merely as being exemplary of the assays which may be performed using the apparatus and method of the present invention. Usually, these tests will require that the blood and plasma be combined with one or more reagents which result in an optically detectable, usually photometrically detectable, change in the plasma. The reagents which are required are well known and amply described in the patent and scientific literature.

The reagents are preferably provided in lyophilized form to increase stability. Ideally, they are provided in the form of lyophilized reagent spheres as described in U.S. Ser. No. 07/747,179, now U.S. Pat. No. 5,413,732, which is incorporated herein by reference.

Figure 1B:
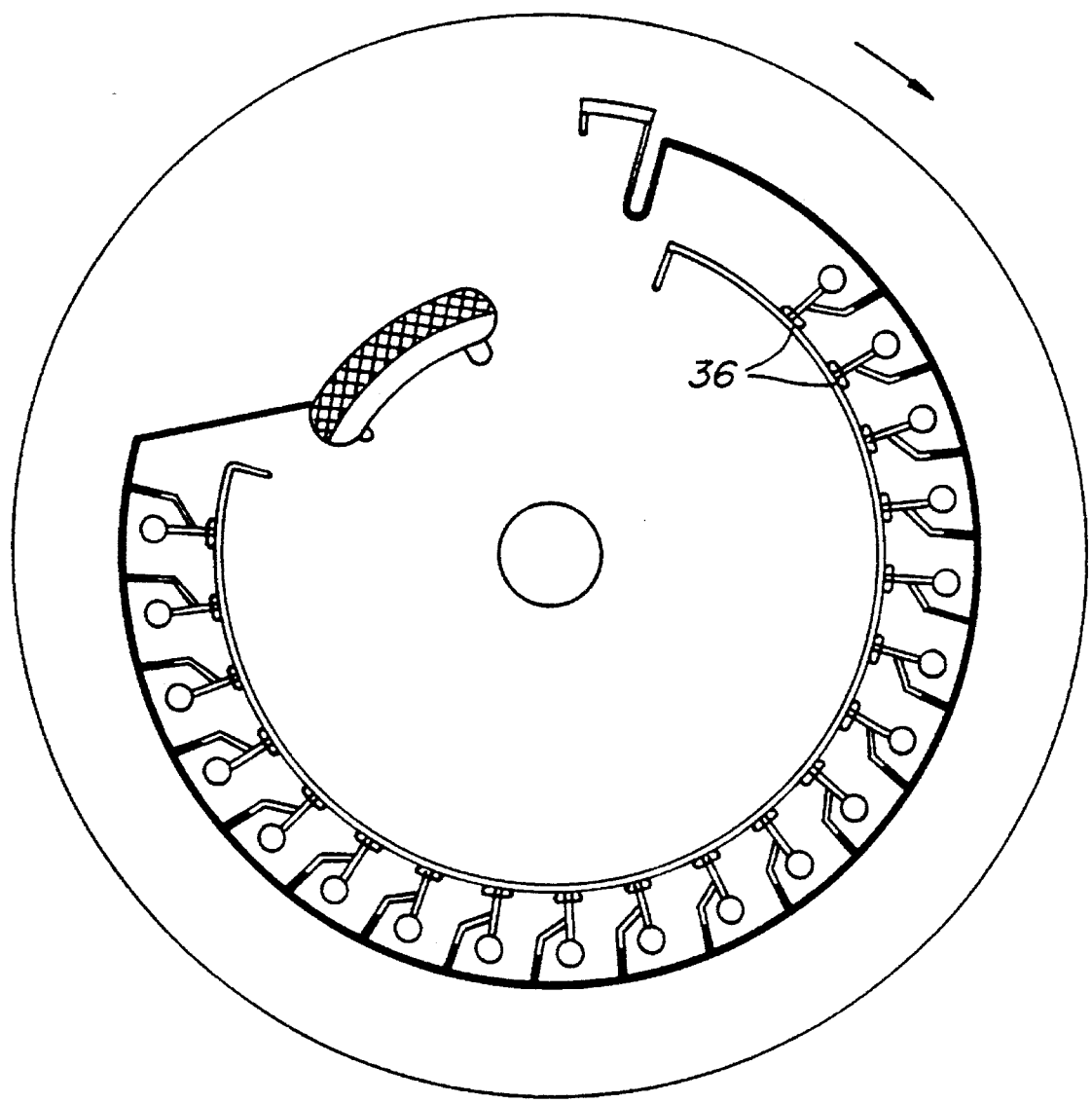
Figure 1C:
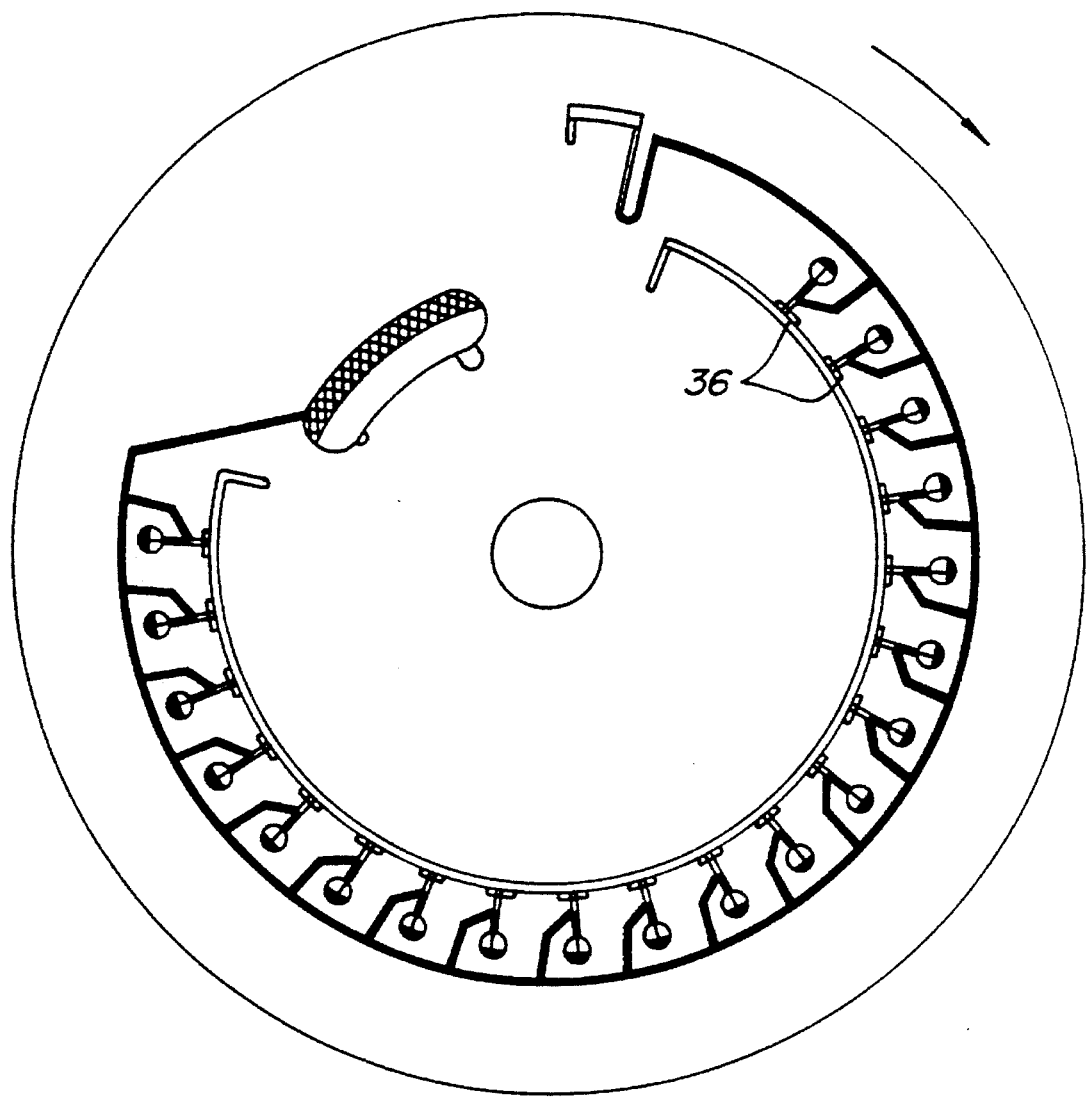
Figure 1D:
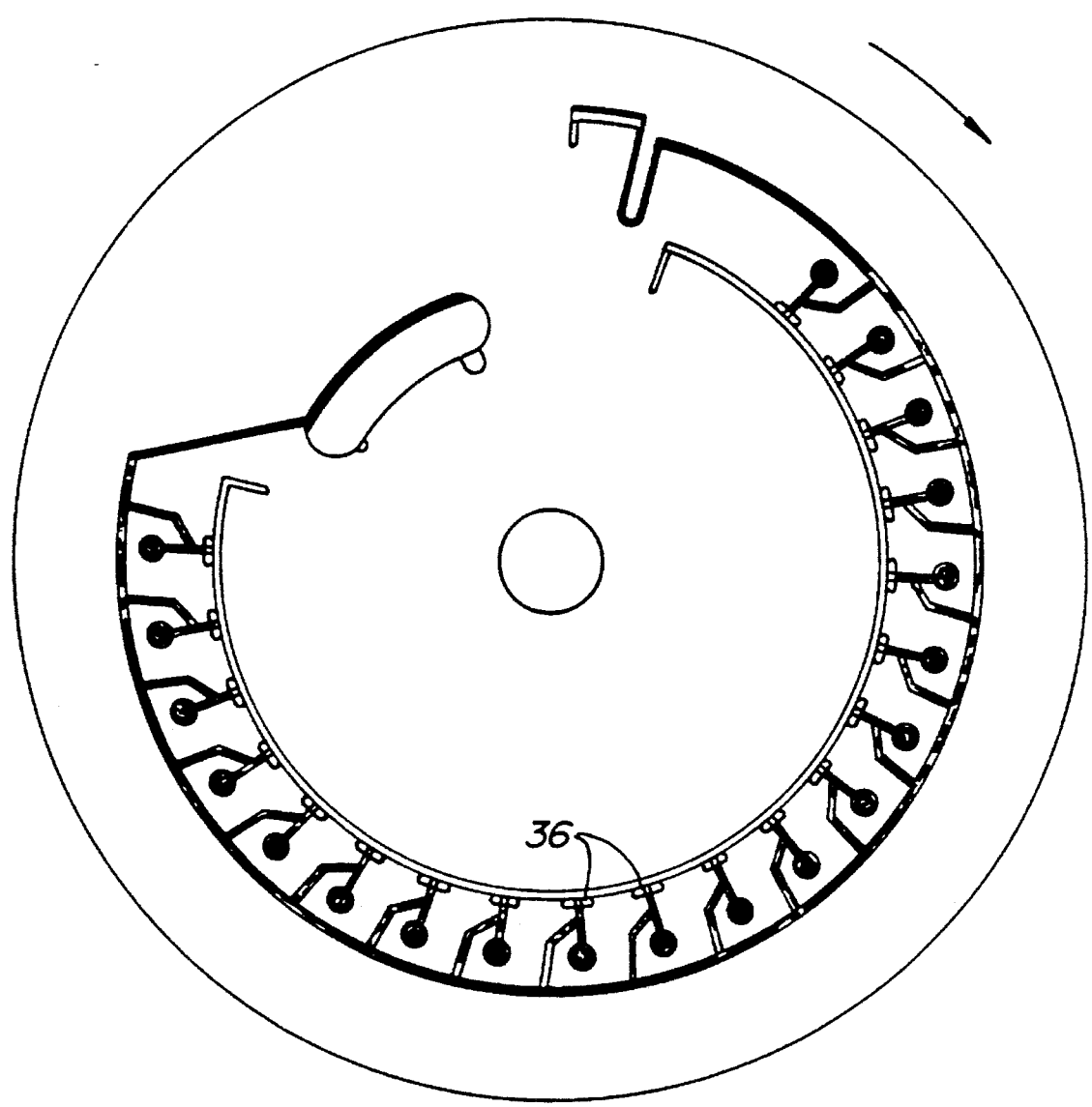
Figure 2:
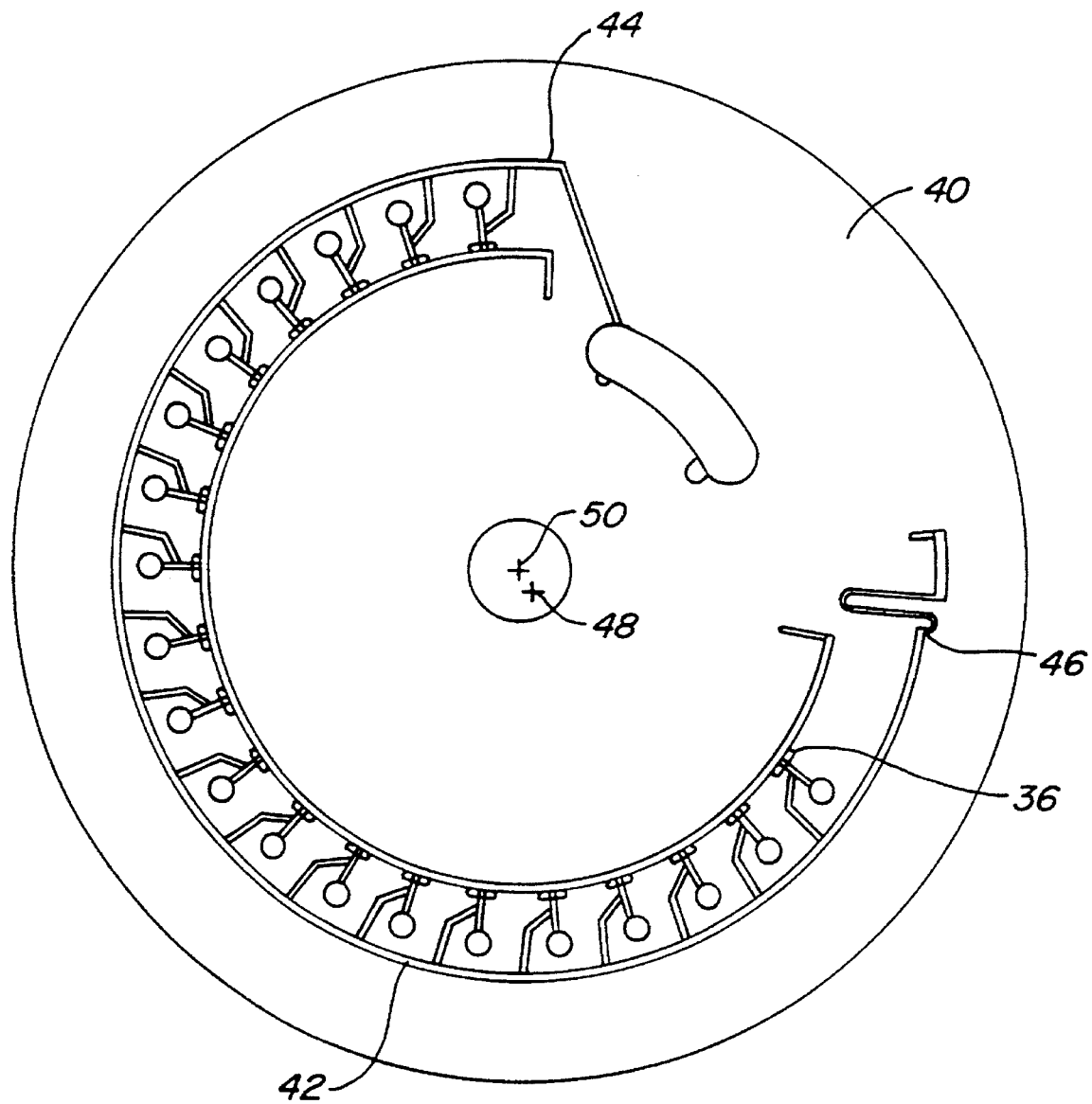
FIG. 2 is a top plan view of a rotor showing the positioning of the liquid manifold such that its axis of rotation is positioned away from the axis of rotation of the rotor.

Referring now to FIGS. 1–3, an analytical rotor comprising the chambers and channels of the present invention can be seen. FIG. 1A illustrates the design of chambers and channels in a rotor 2 of the present invention. As the rotor spins about the axis of rotation 3 in the direction of arrow 4, the sample 32 in the central reservoir 6 flows through the feeding channel 8 under centrifugal force. The rotational speeds to perform most the functions described below must typically generate a centrifugal force of about 170 xg to about 1060 xg, preferably about 380 xg to about 680 xg.

The feeding channel 8 need not be a straight channel as illustrated in FIG. 1A. A siphon can also be used if the timing of flow of sample from the reservoir is desired. If the feeding channel is a siphon, the elbow is positioned no farther from the center of the rotor than the radially most inward point of the metering chamber. As the rotor is spinning the fluid does not flow past the elbow. After the rotor stops, capillary forces "prime" the siphon by pulling fluid just around the elbow. When the rotor is restarted, the combination of centrifugal and capillary forces draw the remaining fluid out of the sample chamber into the manifold.

Alternatively, the siphon can be primed by centrifugal rather than capillary forces. In this embodiment, the elbow is positioned radially such that it primes at a predetermined time.

The feeding channel 8 is connected to one end 10 of the annulate liquid manifold 12 and the sample fills the liquid manifold 12 from the outer radial edge 13 inward. FIG. 1B shows the sample 32 after it has flowed to the opposite end 14 of the liquid manifold 12 and has entered the excess liquid channel 16, which in a preferred embodiment is a siphon 16. The sample then begins to flow radially inward through the inlet channels 20.

The dumping siphon 16 has a cross-sectional area or diameter smaller than that of the liquid manifold 12, inlet channels 20, or feeding channel 8. Alternatively, the excess liquid channel 16 can have the same cross-sectional area as the feeding channel 8 as long as when the excess liquid channel is a siphon there is sufficient sample to prime the siphon and keep it primed while the manifold is emptying. If the sample is plasma or diluted plasma and the channels are rectangular in cross-section, their dimensions are typically as follows: excess liquid channel: 0.150 mm depth, 0.200 mm width; manifold: 0.300 mm depth, 0.500 mm width; inlet channels: 0.150 mm, 0.500 mm; feeding channel: 0.150 mm depth, 0.200 mm width.

The smaller the diameter of a channel, the greater the resistance to flow of fluid through that channel. The resistance to flow in these channels ensures proper filling of the cuvettes 24 as well priming of the dumping siphon 16. In particular, the resistance to flow in the feeding channel 8 must be higher than that in the liquid manifold 12 and sum of the resistance to flow in the inlet channels 20 to ensure simultaneous filling of the cuvettes 24. In addition, the supply of liquid to the siphon 16 must be sufficient to keep the siphon primed. To accomplish this, there should be a "reservoir" of liquid from the manifold and inlet channels which supplies the siphon. The flow rate of the liquid in the liquid manifold and inlet channels, as well as the geometry of the liquid manifold, mainly the increasing radius from the beginning to the end of the manifold, ensure that the siphon stays primed.

A pocket 36 for holding excess liquid is positioned radially inward of each cuvette 24. The pocket 36 is used to trap excess sample 32 and to prevent it from entering the venting manifold. If the venting manifold 28 is placed radially inward of the sample level in the sample reservoir 6, the sample 32 would not enter the venting manifold 28 during the filling process because the sample will find a level equal to that in the sample reservoir 6. In the design shown in FIGS. 1A–D above, the venting manifold 28 is positioned radially outward of the sample reservoir 6. To prevent sample entering the venting manifold 28 when the liquid manifold 12 is filling faster than the excess is being drawn off, the pockets 36 are positioned radially inward of each cuvette 24. The pockets 36 must sized to accommodate any residual sample until the siphon 16 removes the excess sample from the liquid manifold.

In FIG. 1C the sample has flowed through the inlet channels 20 to the U-shaped bends 22 and begun to flow radially outward to the cuvettes 24. The delivery portion 23 of each inlet channel 20 between the U-shaped bend 22 and the cuvette 24 is sized such that gas escapes from the cuvette as the sample enters the cuvettes 24, which are not otherwise vented. Air escaping through the delivery portion 23 continues to flow through venting channels 26 and enters the venting manifold 28 where it is released through air vents 30.

As the rotor continues to spin, the cuvettes 24, the inlet channels 20 and the manifold 12 have been filled (FIG. 1D). At this point, sample has flowed radially inward of the U-shaped bends 22 into the venting channels 26. In addition, the dumping siphon 16 becomes primed because the sample has flowed to the elbow 34. To prevent priming of the siphon 16 before the cuvettes 24 are filled, the U-shaped bends 22 must be spaced radially outward of the elbow 34. After the siphon 16 is primed, centrifugal force draws the sample 32 in the liquid manifold 12, inlet channels 20 and sample reservoir into the excess sample or excess liquid dump 18.

FIG. 1E shows the rotor after the dumping siphon 16 has emptied excess sample. Sample remains in the cuvettes 24 and in the delivery portion 23 of the inlet channels 20 between the cuvettes 24 and the U-shaped bend 22. The sample in each cuvette is now ready for further processing. In the case of cuvettes, the sample will be mixed with appropriate reagents and optically analyzed.

FIG. 2 shows a rotor 40 in which the liquid manifold 42 is positioned such that the first end 44 through which sample is introduced into the liquid manifold 42 is radially inward of the opposite end 46. Thus, the axis of rotation 48 of the liquid manifold 42 is positioned away from the axis of rotation 50 of the rotor. This design facilitates the removal of excess liquid from the liquid manifold 42.

Although the foregoing invention has been described in detail for purposes of clarity of understanding, it will be obvious that certain modifications may be practiced within the scope of the appended claims. For instance, the liquid manifold need not be annulate. The manifold can also be used to deliver aliquots of a sample to chambers in a rotor other than cuvettes. In addition, each cuvette can be individually vented instead of using a venting manifold.

What is claimed is:

1. A method of filling a plurality of chambers in a centrifugal rotor, the method comprising the steps of:

introducing a liquid into a first end of an annulate manifold circumferentially disposed in said rotor and positioned radially outward of a plurality of chambers and a plurality of inlet channels connecting the chambers to the manifold;

spinning the rotor to effect a flow of the liquid through the inlet channels to the chambers, thereby filling the chambers and to effect the flow of liquid through an excess liquid channel, positioned at a second end of the manifold, into an excess liquid dump, positioned radially outward of the manifold, thereby removing excess liquid in the manifold and the inlet channels after the chambers have filled.

2. The method of claim 1, wherein the step of spinning the rotor effects the flow of the liquid generally radially inward to a U-shaped portion in each inlet channel and then generally radially outward to each chamber.

3. The method of claim 1, wherein said introducing is by means of a sample reservoir positioned radially inward of said manifold and a feeding channel connecting said sample reservoir to the first end of the manifold.

4. The method of claim 3, wherein the cross-sectional area of the feeding channel is less than the cross-sectional area of the manifold and inlet channels thereby causing resistance to flow of liquid in the feeding channel to be greater than resistance to flow of liquid in the manifold and the inlet channels.

5. The method of claim 3, wherein the feeding channel is straight.

6. The method of claim 2, wherein said the U-shaped portion of each inlet channel is positioned at the same radial distance from an axis of rotation of said rotor, thereby allowing parallel filling of the chambers.

7. The method of claim 1, wherein the excess liquid channel is a siphon.

8. The method of claim 7, wherein resistance to flow of liquid in the siphon is greater than resistance to flow of liquid into the manifold.

9. The method of claim 1, wherein said rotor further comprises a venting manifold positioned radially inward of the chambers and a plurality of venting channels connecting each chamber to the venting manifold.

10. The method of claim 9, wherein the venting manifold is positioned radially outward of a sample reservoir and a pocket for holding excess liquid is positioned radially inward of each chamber.

11. The method of claim 1, wherein the chambers are cuvettes.

12. The method of claim 11, wherein each cuvette comprises reagents necessary for analysis of blood.

13. The method of claim 1, wherein said liquid is diluted plasma.

* * * * *